United States Patent [19]

Sullivan et al.

[11] Patent Number: 5,824,017

[45] Date of Patent: Oct. 20, 1998

[54] H-BRIDGE CIRCUIT FOR GENERATING A HIGH-ENERGY BIPHASIC WAVEFORM IN AN EXTERNAL DEFIBRILLATOR

[75] Inventors: Joseph L. Sullivan; Lawrence A. Borschowa; Richard C. Nova, all of Kirkland, Wash.

[73] Assignee: Physio-Control Corporation, Redmond, Wash.

[21] Appl. No.: 811,833

[22] Filed: Mar. 5, 1997

[51] Int. Cl.$^6$ .......................................................... A61N 1/39
[52] U.S. Cl. ................................................................ 607/5
[58] Field of Search .................................................. 607/5

[56] References Cited

U.S. PATENT DOCUMENTS

| | | |
|---|---|---|
| 4,800,883 | 1/1989 | Winstrom . |
| 4,821,723 | 4/1989 | Baker, Jr. et al. . |
| 4,850,357 | 7/1989 | Bach, Jr. . |
| 5,083,562 | 1/1992 | de Coriolis et al. . |
| 5,099,844 | 3/1992 | Faupel . |
| 5,431,684 | 7/1995 | Archer et al. . |
| 5,431,686 | 7/1995 | Kroll et al. . |
| 5,441,518 | 8/1995 | Adams et al. . |
| 5,468,254 | 11/1995 | Hahn et al. . |
| 5,470,341 | 11/1995 | Kuehn et al. . |
| 5,591,213 | 1/1997 | Morgan . |
| 5,593,427 | 1/1997 | Gliner et al. . |
| 5,601,612 | 2/1997 | Gliner et al. . |
| 5,607,454 | 3/1997 | Cameron et al. . |

FOREIGN PATENT DOCUMENTS

| | | |
|---|---|---|
| 0 553 864 A2 | 8/1993 | European Pat. Off. . |
| WO 93/16759 | 9/1993 | WIPO . |
| WO 94/27674 | 12/1994 | WIPO . |
| WO 95/05215 | 2/1995 | WIPO . |
| WO 95/09673 | 4/1995 | WIPO . |

OTHER PUBLICATIONS

Gust H. Brady et al., "Multicenter Comparison of Truncated Biphasic Shocks and Standard Damped Sine Wave Monophasic Shocks for Transthoracic Ventricular Defibrillation," *Circulation*, vol. 94, No. 10, Nov. 15, 1996, pp. 2507–2514.

Gust H. Brady et al., "Truncated Biphasic Pulses for Transthoracic Defibrillation," *Circulation*, vol. 91, No. 6, Mar. 15, 1995, pp. 1768–1774.

Richard O. Cummins, M.D., et al., Overview, "Ventricular Fibrillation Automatic External Defibrillators, and the United States Food and Drug Administration: Confrontation Without Comprehension," *Annals of Emergency Medicine*, vol. 26, Nov. 1995, p. 621.

Scott A. Feeser, M.D. et al., Abstract, "Strength—Duration and Probability of Success Curves for Defibrillation with Biphasic Waveforms," *Circulation*, vol. 82, 1990, pp. 2128–2141.

(List continued on next page.)

*Primary Examiner*—William E. Kamm
*Attorney, Agent, or Firm*—Christensen, O'Connor, Johnson & Kindness PLLC

[57] ABSTRACT

An external defibrillator (8) with an output circuit (14) having four legs arrayed in the form of an "H" (an "H-bridge") is disclosed. Each leg of the output circuit contains a solid-state switch (31, 32, 33, 34). By selectively switching on pairs of switches in the H-bridge, a biphasic defibrillation pulse may be applied to a patient. The switches in three of the legs of the H-bridge output circuit are preferably silicon controlled rectifiers (SCRs). Gate drive circuits (51, 53, 54) are coupled to the SCRs to bias the SCRs with a voltage that allows the SCRs to remain turned-on even when conducting low current. The switch in the fourth leg is preferably a pair of insulated gate bipolar transistors (IGBTs) coupled in series. A gate drive circuit (52) is coupled to the gate of the IGBTs to provide a slow turn-on and a fast turn-off of the IGBTs. The gate drive circuit (52) also biases the IGBTs with a sufficient voltage to allow the IGBTs to withstand a shorted discharge of the external defibrillator through the output circuit.

47 Claims, 2 Drawing Sheets

OTHER PUBLICATIONS

Bradford E. Gliner et al., "Transthoracic Defibrillation of Swine with Monophasic and Biphasic Waveforms," *Circulation,* vol. 92, No. 6, Sep. 15, 1995, pp. 1634–1643.

Mark W. Kroll, "A Minimal Model of the Single Capacitor Biphasic Defibrillation Waveform," *PACE,* vol. 17, Nov. 1994, Part I, pp. 1782–1792.

Anthony S.L. Tang, M.D. et al., Abstract, "Ventricular Defibrillation Using Biphasic Waveforms: The Importance of Phasic Duration," *Journal of American College of Cardiology,* vol. 13, 1989, pp. 207–214.

Gregory P. Walcott et al., "Choosing the Optimal Monophasic and Biphasic Waveforms for Ventricular Defibrillation," *Journal of Cardiovascular Electrophysiology,* vol. 6, No. 9, Sep. 1995, pp. 737–750.

5,824,017

H-BRIDGE CIRCUIT FOR GENERATING A HIGH-ENERGY BIPHASIC WAVEFORM IN AN EXTERNAL DEFIBRILLATOR

FIELD OF THE INVENTION

This invention relates generally to apparatus for generating defibrillation waveforms, and more particularly to a circuit for generating a biphasic defibrillation waveform in an external defibrillator.

BACKGROUND OF THE INVENTION

One of the most common and life-threatening medical conditions is ventricular fibrillation, a condition where the human heart is unable to pump the volume of blood required by the human body. The generally accepted technique for restoring a normal rhythm to a heart experiencing ventricular fibrillation is to apply a strong electric pulse to the heart using an external cardiac defibrillator. External cardiac defibrillators have been successfully used for many years in hospitals by doctors and nurses, and in the field by emergency treatment personnel, e.g., paramedics.

Conventional external cardiac defibrillators first accumulate a high-energy electric charge on an energy storage capacitor. When a switching mechanism is closed, the stored energy is transferred to a patient in the form of a large current pulse. The current pulse is applied to the patient via a pair of electrodes positioned on the patient's chest. The switching mechanism used in most contemporary external defibrillators is a high-energy transfer relay. A discharge control signal causes the relay to complete an electrical circuit between the storage capacitor and a wave shaping circuit whose output is connected to the electrodes attached to the patient.

The relay used in contemporary external defibrillators has traditionally allowed a monophasic waveform to be applied to the patient. It has recently been discovered, however, that there may be certain advantages to applying a biphasic rather than a monophasic waveform to the patient. For example, preliminary research indicates that a biphasic waveform may limit the resulting heart trauma associated with the defibrillation pulse.

The American Heart Association has recommended a range of energy levels for the first three defibrillation pulses applied by an external defibrillator. The recommended energy levels are: 200 joules for a first defibrillation pulse; 200 or 300 joules for a second defibrillation pulse; and 360 joules for a third defibrillation pulse, all within a recommended variance range of no more than plus or minus 15 percent according to standards promulgated by the Association for the Advancement of Medical Instrumentation (AAMI). These high energy defibrillation pulses are required to ensure that a sufficient amount of the defibrillation pulse energy reaches the heart of the patient and is not dissipated in the chest wall of the patient.

While generating a biphasic waveform would be desirable in an external defibrillator, to date output circuits for generating a biphasic waveform have not been developed that can reliably and simply switch the higher voltages required in an external defibrillator. Some implantable defibrillators, such as those shown in U.S. Pat. Nos. 5,083,562 and 4,880,357, use a bridge circuit with multiple silicon-controlled rectifiers (SCRs) to generate a biphasic waveform. Because implantable defibrillators only apply a low energy defibrillation pulse having a maximum energy of 25 joules, however, the output circuit in implantable defibrillators is not adaptable for use in the external defibrillator. A 200 joule energy pulse applied to an implantable defibrillator bridge circuit would overload the bridge circuit components and cause the circuit to fail.

The present invention is directed to providing apparatus that overcome the foregoing and other disadvantages. More specifically, the present invention is directed to an output circuit for an external defibrillator that is capable of applying a high-energy biphasic defibrillation pulse to a patient.

SUMMARY OF THE INVENTION

An external defibrillator having an output circuit that allows a biphasic defibrillation pulse to be discharged to a patient from an energy storage device, preferably an energy storage capacitor, is disclosed. The output circuit includes four legs arrayed in the form of an "H" (hereinafter the "H-bridge output circuit"). Each leg of the output circuit contains a solid-state switch. By selectively switching on pairs of switches in the H-bridge output circuit, a biphasic defibrillation pulse may be applied to the patient.

In accordance with one aspect of the invention, the switches in three of the legs of the H-bridge output circuit are silicon controlled rectifiers (SCRs). Preferably, only a single SCR is used in each leg. The switches in the fourth leg are insulated gate bipolar transistors (IGBTs). The use of single SCR switches simplifies the circuit as compared to the use of semiconductor modules that are large and expensive or as compared to the use of lower voltage parts which must be stacked. The use of three SCR legs further reduces the size, weight, and cost of the H-bridge output circuit in comparison with an implementation using two SCR and two IGBT legs.

In accordance with another aspect of the invention, the H-bridge output circuit is capable of conducting a biphasic waveform of 200 or more joules from the energy storage capacitor to the patient. Preferably, the H-bridge output circuit is capable of conducting a biphasic waveform equal to 360 joules, the industry standard for monophasic waveforms and the recommended level for a third defibrillation pulse by the American Heart Association. To store sufficient energy for such a biphasic defibrillation pulse, the size of the energy storage capacitor falls within a range from 150 uF to 200 uF.

Moreover, in addition to being able to conduct a high energy defibrillation pulse of 200 to 360 joules, the H-bridge output circuit is also capable of conducting a low energy defibrillation pulse for internal applications with an energy as low as 1 to 50 joules. Low energy defibrillation pulses are required when, for example, internal paddles are coupled to the defibrillator for use in surgery to directly defibrillate the heart. To allow the delivery of a low energy defibrillation pulse, the output circuit switches in three of the legs are driven by gate drive circuits which provide a pulsed control signal to the gates of the switches. The pulsed control signal on the gates allows the high voltage switches to remain conducting even when conducting very low currents.

In accordance with another aspect of the invention, the output circuit switches are selected to have sufficient current conducting capability to allow the switches in two of the legs on the same side of the H-bridge to provide a shorted path for the discharge of unwanted energy from the energy storage capacitor. The use of two legs on one side of the H-bridge to discharge the capacitor eliminates the need for an additional discharge circuit.

In accordance with still another aspect of the invention, a gate drive circuit biases on the IGBTs in the fourth leg with a sufficient voltage over a short interval to allow the leg to conduct approximately 400 amps of current without being damaged. Biasing the IGBTs in this manner allows the IGBTs to withstand a shorted discharge in the event the shock paddles are accidentally placed together, or in the event that there is a short in the circuit.

In accordance with yet another aspect of the invention, the gate drive circuit provides a slow turn-on and fast turn-off of the IGBTs. The slow turn-on avoids jolting an electrically coupled SCR on one of the other H-bridge output circuit legs into a conducting state. The fast turn-off reduces the exposure of the IGBTs to potentially damaging high voltages that can occur across one IGBT when the other IGBT is inadvertently turned off first. The IGBT gate drive circuitry therefore reduces the size of the high-voltage parts that are necessary to protect the IGBTs.

It will be appreciated that the disclosed H-bridge output circuit is advantageous in that it allows either a high-energy biphasic waveform or a low-energy biphasic waveform to be generated by an external defibrillator and applied to a patient.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
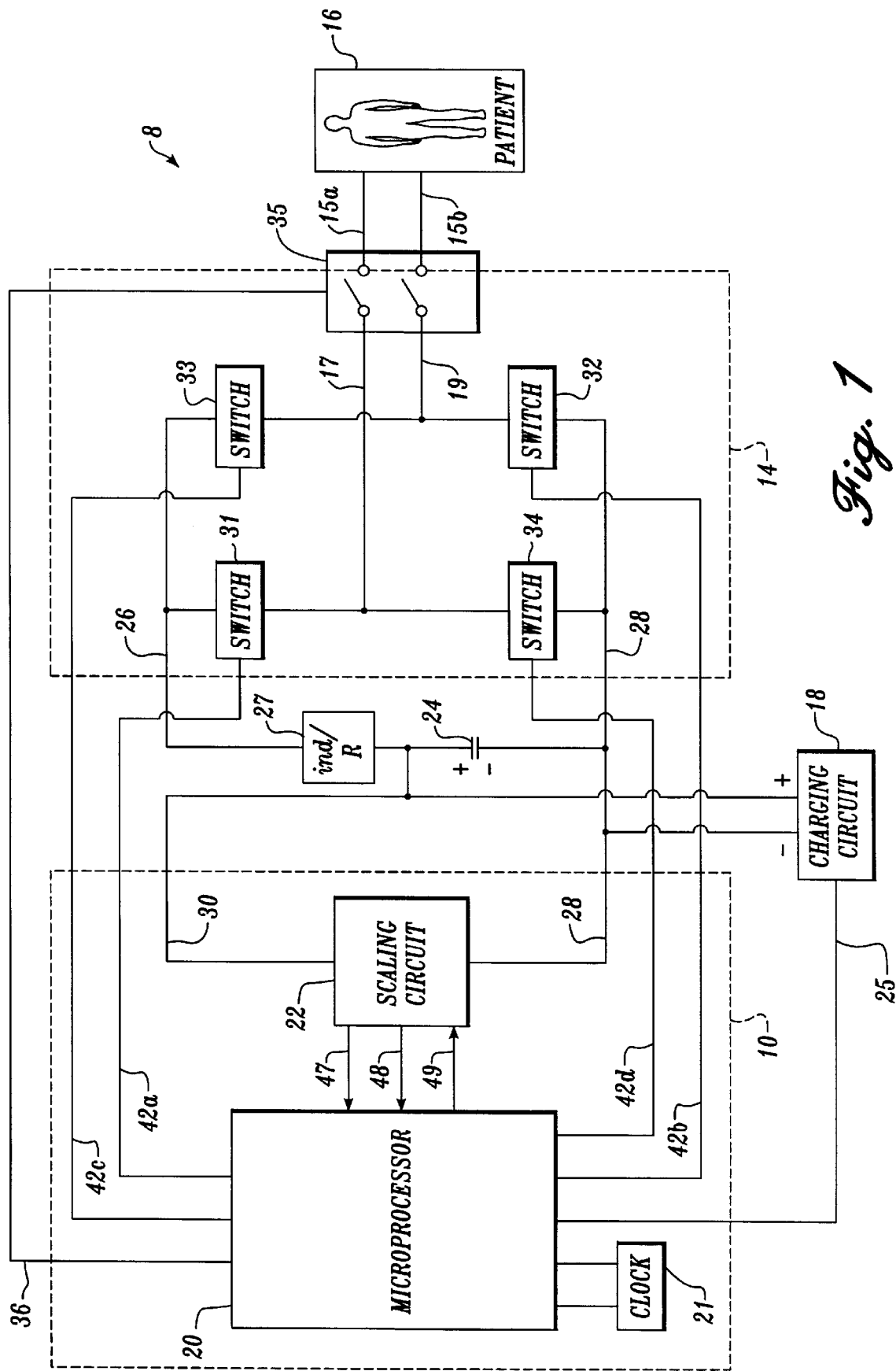
FIG. 1 is a block diagram of an external defibrillator having an output circuit suitable for delivering a high-energy biphasic defibrillation pulse to a patient.

FIG. 1 is a block diagram of an external defibrillator 8 that is connected to a patient 16. The defibrillator includes a microprocessor 20 that is connected to an energy storage capacitor 24 via a charging circuit 18. During the operation of the defibrillator, the microprocessor controls the charging circuit 18 by a signal on a control line 25 to charge the energy storage capacitor to a desired voltage level. To monitor the charging process, the microprocessor is connected to a scaling circuit 22 by a pair of measurement lines 47 and 48, and by a control line 49. The scaling circuit 22 is connected to the energy storage capacitor 24 by a bridge line 28, which connects to the negative lead of the capacitor, and by a line 30, which connects to the positive lead of the capacitor. A clock 21 is also connected to the microprocessor 20.

The scaling circuit 22 is used to step down the voltage across the energy storage capacitor 24 to a range that may be monitored by the microprocessor. The scaling circuit 22 is described briefly below and in more detail in an application entitled "Method and Apparatus for Verifying the Integrity of an Output Circuit Before and During Application of a Defibrillation Pulse" (attorney docket no. PHYS19375), filed concurrently herewith and hereby incorporated by reference. The energy storage capacitor 24 can be charged to a range of voltage levels, with the selected level depending on the patient and other parameters. Preferably, the size of the energy storage capacitor falls within a range from 150 uF to 200 uF. In order to generate the necessary defibrillation pulse for external application to a patient, the energy storage capacitor is charged to between 100 volts and 2,200 volts. To detect small percentage changes in the selected voltage level of the energy storage capacitor 24, the scaling circuit is adjustable to measure different voltage ranges. The adjusted output is measured by the microprocessor 20 on measurement line 48.

After charging to a desired level, the energy stored in the energy storage capacitor 24 may be delivered to the patient 16 in the form of a defibrillation pulse. An output circuit 14 is provided to allow the controlled transfer of energy from the energy storage capacitor to the patient. The output circuit 14 includes four switches 31, 32, 33, and 34, each switch on a leg of the output circuit arrayed in the form of an "H" (hereinafter the "H-bridge" output circuit). Switches 31 and 33 are coupled through a protective component 27 to the positive lead of the energy storage capacitor 24 by a bridge line 26. The protective component 27 limits the current and voltage changes from the energy storage capacitor 24, and has both inductive and resistive properties. Switches 32 and 34 are coupled to the energy storage capacitor 24 by a bridge line 28. The patient 16 is connected to the left side of the H-bridge by an apex line 17, and to the right side of the H-bridge by a sternum line 19. As depicted in FIG. 1, the apex line 17 and the sternum line 19 are connected to electrodes 15a and 15b, respectively, by a patient isolation relay 35. The microprocessor 20 is connected to the switches 31, 32, 33, and 34 by control lines 42a, 42b, 42c, and 42d, respectively, and to the patient isolation relay 35 by control line 36. Application of appropriate control signals by the microprocessor over the control lines causes the switches to be opened and closed, and the output circuit 14 to conduct energy from the energy storage capacitor 24 to the patient.

Figure 2:
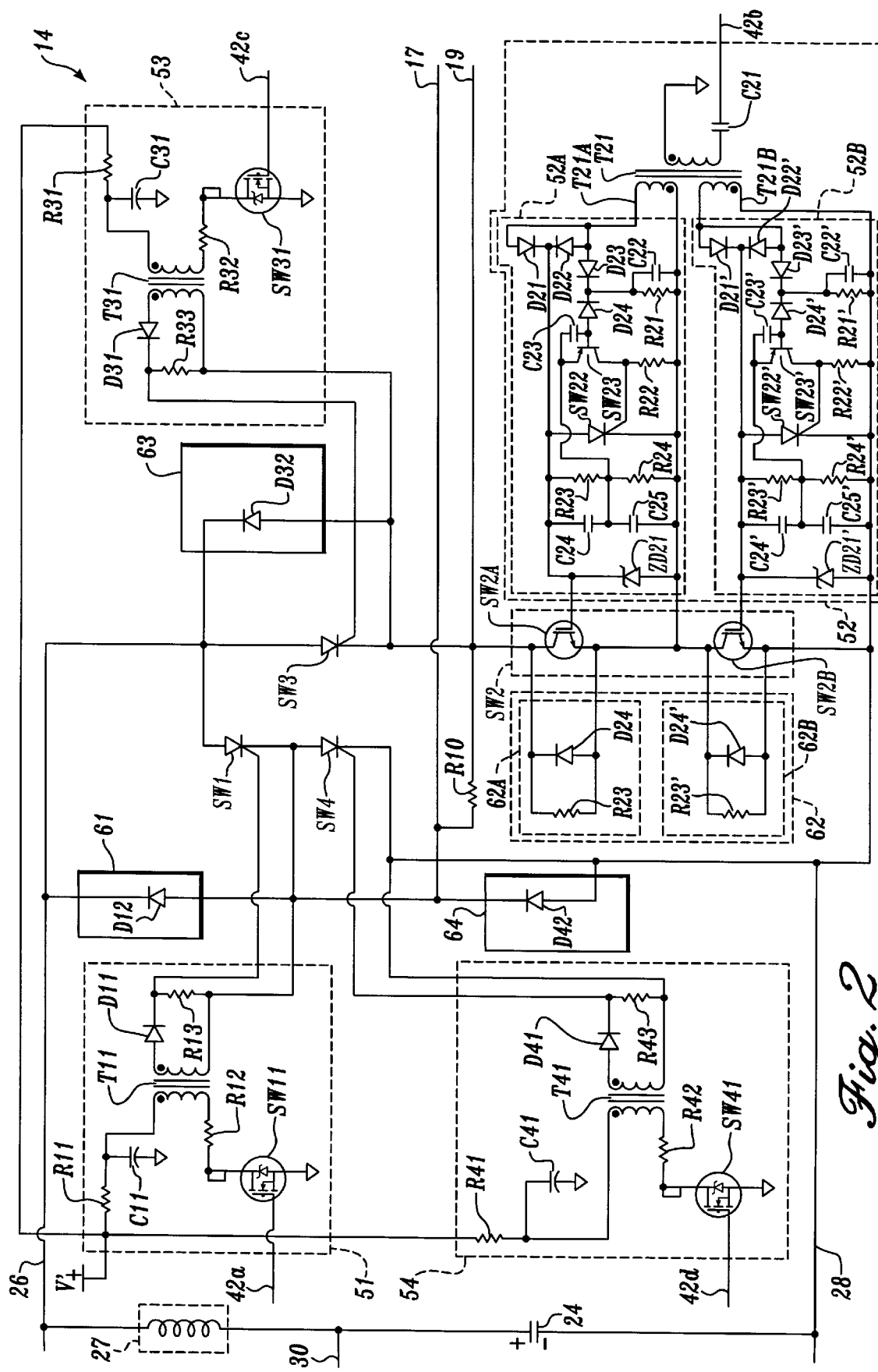
FIG. 2 is a schematic diagram of the preferred embodiment of the output circuit of FIG. 1.

A preferred construction of the output circuit 14 is shown in FIG. 2. The output circuit relies on four output switches SW1 to SW4 to conduct energy from the energy storage capacitor 24 to the patient. Switches SW1, SW3 and SW4 are semiconductor switches, preferably silicon controlled rectifiers (SCRs). Switch SW2 is a series combination of switches SW2A and SW2B, preferably both insulated gate bipolar transistors (IGBTs). Two IGBTs are required because the limitations of IGBT switch technology are such that the maximum working voltage of presently available IGBTs is not sufficient to withstand the maximum voltage that may occur across switch SW2 in output circuit 14. Switch SW2 is therefore constructed with two IGBT switches that are connected in series so that the voltage across the entire switch SW2 is divided between the two IGBT switches. Those skilled in the art will appreciate that a single IGBT may be used in the output circuit, should an IGBT having a sufficient voltage rating become available. The four output switches SW1 to SW4 can be switched from an off (non-conducting) to an on (conducting) condition.

Defibrillator 8 generates a biphasic defibrillation pulse for application to the patient 16. When the energy storage capacitor 24 is charged to a selected energy level and the patient isolation relay 35 is closed, the switches SW1 and SW2 are switched on so as to connect the energy storage capacitor with the apex line 17 and sternum line 19 for the application of a first phase of a defibrillation pulse to the patient. The stored energy travels from the positive terminal of the energy storage capacitor 24 on line 26, through switch SW1 and apex line 17, across the patient 16, and back through sternum line 19 and switch SW2 to the negative terminal of the capacitor on line 28. The first phase of the biphasic pulse is therefore a positive pulse from the apex to the sternum of the patient.

Before the energy storage capacitor 24 is completely discharged, the switch SW2 is biased off to prepare for the application of the second phase of the biphasic pulse. Once the switch SW2 is biased off, switch SW1 will also become non-conducting because the voltage across the SCR falls to zero.

After the end of the first phase of the biphasic defibrillation pulse, switches SW3 and SW4 are switched on to start the second phase of the biphasic pulse. Switches SW3 and SW4 provide a path to apply a negative defibrillation pulse to the patient 16. The energy travels from the positive terminal of the energy storage capacitor 24 on line 26, through switch SW3 and sternum line 19, across the patient 16, and back through apex line 17 and switch SW4 to the negative terminal of the energy storage capacitor on line 28. The polarity of the second phase of the defibrillation pulse is therefore opposite in polarity to the first phase of the biphasic pulse. The end of the second phase of the biphasic pulse is truncated by switching on switch SW1 to provide a shorted path for the remainder of the capacitor energy through switches SW1 and SW4. After the second phase is truncated, all four of the switches SW1 to SW4 are switched off and the patient isolation relay 35 is opened. The energy storage capacitor 24 may then be recharged to prepare the defibrillator to apply another defibrillation pulse.

As described above, the four output switches SW1 to SW4 can be switched from an off (nonconducting) state to an on (conducting) state by application of appropriate control signals on control lines 42a, 42b, 42c, and 42d. In order to allow the SCRs and IGBTs to switch the high voltages in an external defibrillator, special switch driving circuits 51, 52, 53 and 54 are coupled to switches SW1 to SW4, respectively. The control lines 42a, 42b, 42c, and 42d are connected to the switch driving circuits 51, 52, 53, and 54, to allow the microprocessor to control the state of the switches.

Switch driving circuits 51, 53 and 54 are identical. For purposes of this description, therefore, only the construction and operation of switch driving circuit 51 will be described. Those skilled in the art will recognize that switch driving circuits 53 and 54 operate in a similar manner.

Switch driving circuit 51 includes control switch SW11, resistors R11, R12, and R13, capacitor C11, diode D11 and high-voltage transformer T11. Resistor R11 is connected between the positive voltage supply V'+ and the dotted end of the primary winding of transformer T11, and capacitor C11 is connected between ground and the dotted end of the primary winding of transformer T11. Resistor R12 is connected between the non-dotted end of the primary winding of transformer T11 and the drain of the control switch SW11. Resistors R11 and R12 and capacitor C11 limit and shape the current and voltage waveforms across the primary winding of the transformer T11. The source of the control switch SW11 is connected to ground, and the gate of control switch SW11 is connected to control line 42a.

On the secondary winding side of transformer T11, the anode of diode D11 is connected to the dotted end of the secondary winding of transformer T11, and the cathode of diode D11 is connected to the gate of the SCR switch SW1. Resistor R13 is connected between the cathode of diode D11 and the non-dotted end of the secondary winding of the transformer T11. The non-dotted end of the secondary winding of transformer T11 is connected to the cathode of the SCR switch SW1.

To turn on switch SW1, an oscillating control signal, preferably a pulse train, is provided on control line 42a. The pulse train control signal repeatedly turns control switch SW11 on and off, producing a changing voltage across the primary winding of the transformer T11. The voltage is stepped down by the transformer T11 and rectified by the diode D11 before being applied to the SCR switch SW1. In the preferred embodiment, a 10% duty cycle pulse train on the control line 42a has been found to be adequate to maintain the SCR switch SW1 in a conducting state. As long as the control signal is applied to the switch driving circuit 51, the switch SW1 will remain in the conducting state. The switch SW1 remains in the conducting state even when conducting only very low currents, such as the current associated with a low-energy defibrillation pulse.

A different switch driving circuit is required to turn on the IGBT switches of switch SW2. Switch driving circuit 52 includes a capacitor C21, a transformer T21, and two identical switch driving circuits 52A and 52B, each circuit corresponding to one of the IGBTs. On the primary winding side of the transformer T21, capacitor C21 is connected between the control line 42b and the non-dotted end of the primary winding of the transformer T21. The dotted end of the primary winding of the transformer T21 is connected to ground.

Transformer T21 has two secondary windings T21A and T21B, one for each of the switch driving circuits 52A and 52B. Switch driving circuits 52A and 52B are identical, and therefore only the construction and operation of switch driving circuit 52A will be described. Switch driving circuit 52A includes diodes D21, D22, D23, and D24, Zener diode ZD21, capacitors C22, C23, C24, and C25, resistors R21, R2, R23, and R24, a PNP switch SW23, and an SCR switch SW22.

The anodes of the diodes D21, D22, and D23 are connected to the non-dotted end of the secondary winding T21A of the transformer T21. The cathodes of diodes D21 and D22 are connected to the gate of the IGBT switch SW2A. The resistor R21 and capacitor C22 are connected between the dotted end of the secondary winding T21A of the transformer T21 and the cathode of diode D23. The anode of the SCR switch SW22 and the cathode of Zener diode ZD21 are connected to the gate of the IGBT switch SW2A. The cathode of the SCR switch SW22 and the anode of the Zener diode ZD21 are connected to the dotted end of the secondary winding T21A of the transformer T21, and also to the emitter of the IGBT switch SW2A.

The resistor R23 and the capacitor C24 are connected between the gate of the IGBT switch SW2A and the emitter of the PNP switch SW23. The resistor R24 and the capacitor C25 are connected between the emitter of the PNP switch SW23 and the dotted end of the secondary winding T21A of the transformer T21. The gate of the SCR switch SW22 is connected to the collector of the PNP switch SW23. The resistor R22 is connected between the collector of the PNP switch SW23 and the dotted end of the secondary winding T21A of the transformer T21. The capacitor C23 is connected between the emitter and the base of the PNP switch SW23. The anode of the diode D24 is connected to the base of the PNP switch SW23, and the cathode of the diode D24 is connected to the cathode of the diode D23.

To turn on the IGBT switch SW2A, an oscillating control signal, preferably a pulse train, is provided on control line 42b. The pulse train control signal is stepped up in voltage by the transformer T21 and applied to the input of switch driving circuit 52A. During a positive pulse of the control signal on control line 42b, diodes D21 and D22 rectify the current that travels through the secondary winding T21A to charge capacitors C24 and C25. As will be discussed in more detail below, some current also travels through diode D23 to charge capacitor C22.

Capacitor C21 limits the current in the primary winding of the transformer T21, which correspondingly limits the current in the secondary winding T21A. The secondary winding current determines the charging time of the capacitors C24 and C25. Since the voltage across the capacitors C24 and C25 is also the voltage on the gate of the IGBT switch SW2A, a slow accumulation of voltage on the capacitors C24 and C25 therefore results in a slow turn on of the IGBT switch SW2A. The charging current is selected so that the IGBT switch SW2A is turned on relatively slowly when compared to the fast turn on of the SCR switches SW1, SW3, and SW4. A slow turn-on for the IGBT switch SW2A is desirable because the IGBT switches are on the same side of the H-bridge output circuit 14 as SCR switch SW3. SCR switch SW3 is controlled by the control signal on control line 42c, but due to the nature of SCR switches, the SCR switch may be accidentally turned on regardless of the signal on control line 42c if a rapid voltage change occurs across SCR switch SW3. If IGBT switches SW2A and SW2B were therefore turned on too quickly, the resulting rate of change of the voltage across SCR switch SW3 might cause it to turn on accidentally.

Zener diode ZD21 protects the IGBT switch SW2A by regulating the maximum voltage across the capacitors C24 and C25. Without Zener diode ZD21, the voltage on the gate of IGBT switch SW2A would rise to a level that would damage IGBT switch SW2A.

Also during the positive pulse of the pulse train control signal on control line 42b, diode D23 rectifies the current that travels through the secondary winding T21A to charge capacitor C22. The charge on capacitor C22, which is replenished on each positive pulse of the pulse train control signal, maintains the voltage across the base of the PNP switch SW23 above the turn-on level for the PNP switch. The PNP switch SW23 turns on if the base voltage on the switch drops below a threshold level. As will be described below, the PNP switch SW23 is only turned on when the IGBT switch SW2A is to be turned off. Capacitor C23 and diode D24 are also provided to prevent PNP switch SW23 from turning on. Capacitor C23 serves as a high frequency filter to prevent the high frequency driving pulses of the switch driving circuit 52A from causing the PNP switch to spuriously turn on. Diode D24 prevents a large negative base-emitter voltage from occurring which could cause the PNP switch to enter reverse breakdown.

Since some discharging of the capacitor C22 occurs through resistor R21 between positive pulses of the control signal on control line 42b, resistor R21 must be large enough to limit the discharging current flow from the capacitor C22 between the pulses. Limiting the current flow prevents the voltage on capacitor C22 from dropping below the threshold level sufficient to turn on PNP switch SW23 between pulses of the control signal. Then, during a positive pulse of the pulse train control signal on control line 42b, the charging of capacitor C22 must be sufficient to counteract the discharging that occurred since the previous positive pulse so as to return the capacitor C22 to its fully charged level by the end of the positive pulse.

In the preferred embodiment, a 2 MHz pulse train control signal with a 25% duty cycle on the control line 42b has been found to be adequate to maintain the conducting state of the IGBT switches SW2A and SW2B. The switches will remain conducting as long as the control signal is present, and regardless of the current flowing through the switches.

The maximum current that may generally occur in the output circuit 14 results from the undesirable situation where a user of the defibrillator places the two shock paddles directly in contact with one another. When this happens, a short circuit is created between the apex line 17 and the sternum line 19. During a short circuit, a brief current of up to 400 amps can result. To accommodate the short circuit current without damaging IGBT switches SW2A and SW2B, the IGBT switches SW2A and SW2B are biased by a 30 V gate voltage. Biasing the IGBTs at this voltage level is successful since the IGBT switches are used in a pulsed manner. If the IGBT switches were driven continuously for long periods of time with 30 V on their gates, they might be damaged, but in the defibrillator output circuit they are only driven at this level for very brief intervals.

In contrast to the slow turn-on of the IGBT switches SW2A and SW2B, the turn-off of the IGBT switches is performed relatively quickly. The IGBT switches may be quickly turned off because at turn-off there is no concern that the sensitive SCR switches will accidentally turn on. In addition, a fast turn-off is desirable to reduce the time that an IGBT switch would be subjected to a high voltage if one of the IGBT switches is inadvertently turned off before the other.

The IGBT switches are turned off when the pulse train control signal on the control line 42b is removed. Once positive voltage pulses are no longer being induced in the secondary windings of the transformer T21, the driving circuits 52A and 52B begin the turn-off process. Again, the turn-off process will only be described with respect to driving circuit 52A since the circuits are identical.

During the turn-off process, capacitor C22 begins discharging through resistor R21. Since the RC time constant of capacitor C22 and resistor R21 is much smaller than the RC time constant of capacitors C24 and C25 and resistors R23 and R24, the discharging of the capacitor C22 occurs much more quickly than the discharging of the capacitors C24 and C25. When the voltage on the capacitor C22 drops below a threshold voltage level, PNP switch SW23 is turned on. The threshold voltage level is equivalent to the base turn-on voltage of the PNP switch SW23, plus the voltage drop across diode D24. Once PNP switch SW23 is turned on, discharge current from the capacitor C25 begins to flow through the switch. As the current increases, the voltage across resistor R22 correspondingly increases. When the voltage across resistor R22 reaches a sufficient voltage level, SCR switch SW22 is turned on, providing a shorted path for the remainder of the energy stored in capacitors C24 and C25. The rapid discharge of the capacitors C24 and C25 causes a corresponding rapid drop in the gate voltage of the IGBT switch SW2A, quickly turning off the switch. Resistors R23 and R24 are provided across capacitors C24 and C25 to control the voltage division across the capacitors.

It will be appreciated that the special driving circuits 52A and 52B allow the IGBTs to be used in an external defibrillator where extremely high voltages must be switched in the presence of SCRs. The driving circuits minimize the number of components required to switch a defibrillation pulse of 200 or more joules. In addition to conducting high currents associated with high-energy defibrillation pulses, the IGBTs are also able to conduct very low currents that are associated with defibrillation pulses of less than 50 joules.

As shown in FIG. 2, each switch SW1 to SW4 is also connected in parallel with a switch protection circuit 61, 62, 63, and 64, respectively. The switch protection circuits are designed to prevent spurious voltage spikes from damaging the switches in the output circuit 14. Switch protection circuits 61, 63 and 64 are identical and therefore only the construction and operation of switch protection circuit 61 will be described. Switch protection circuit 61 includes a diode D12. The cathode of the diode D12 is connected to the anode of SCR switch SW1, and the anode of the diode D12 is connected to the cathode of SCR switch SW1. Diode D12 protects SCR switch SW1 against negative inductive spikes that may occur due to cable or load inductance.

Switch protection circuit 62 includes two identical switch protection circuits 62A and 62B, which protect IGBT switches SW2A and SW2B, respectively. Since switch protection circuits 62A and 62B are identical, only the construction and operation of switch protection circuit 62A will be described. Switch protection circuit 62A includes a diode D24 and a resistor R23. The resistor R23 is connected between the collector and the emitter of IGBT switch SW2A. The cathode of diode D24 is connected to the collector of IGBT switch SW2A, and the anode of diode D24 is connected to the emitter of IGBT switch SW2A.

Diode D24 operates similarly to diode D12 as described above in that it protects IGBT switch SW2A against negative inductive spikes. Resistor R23 (in conjunction with resistor R23') ensures that the voltage across the two IGBT switches SW2A and SW2B is equally divided when the output circuit 14 is at rest. Dividing the voltage across the two IGBT switches SW2A and SW2B is important due to the limitations of present IGBT technology, which limits the rating of each IGBT switch to 1200 V. In a system where the total maximum voltage is 2200 V, the maximum voltage ratings are therefore obeyed by dividing the maximum voltage across each IGBT switch.

Additional protection to the switches is provided by the protective component 27, which has both inductive and resistive properties. The protective component 27 limits the rate of change of the voltage across, and current flow to, the SCR switches SW1, SW3, and SW4. Too high of a rate of change of the voltage across an SCR switch is undesirable because it can cause the SCR switch to inadvertently turn on. For example, since SCR switches SW1 and SW4 are on the same side of the H-bridge output circuit 14, any time SCR switch SW4 is abruptly turned on, a rapid voltage change may also result across SCR switch SW1. To prevent rapid voltage changes, protective component 27 reduces the rate of change of the voltage across SCR switch SW1 when SCR switch SW4 is turned on. Also, too high of a current flow can damage the switches SW1, SW3 and SW4, and protective component 27 limits the current flow in the output circuit 14. The use of protective component 27 therefore reduces the need for additional protective components that would otherwise need to be coupled to the switches SW1, SW3 and SW4.

It will be appreciated that the greatest advantage of the output circuit 14 described above is that it allows an external defibrillator to generate and apply a high-energy biphasic waveform to a patient. For prior defibrillators providing a monophasic waveform, the standard energy level in the industry for the discharge has been greater than 200 joules. The above described circuit allows the same amount of energy (more than 200 joules) to be delivered to the patient in a biphasic waveform, thereby resulting in a greater certainty of defibrillation effectiveness for a broader range of patients. At the same time, the circuit incorporates special driving circuitry to allow even very low energy biphasic waveforms (less than 50 joules) to be delivered to the patient.

While the preferred embodiment of the invention has been illustrated and described, it will be apparent that various changes can be made therein without departing from the spirit and scope of the invention. For example, control lines 42c and 42d and control switches SW31 and SW41 could be replaced by a single control line and control switch to activate switch driving circuits 53 and 54. Also, while the preferred construction for switches 31, 32, 33, and 34 is described above, it will be appreciated that other switch constructions may be envisioned, such as replacing switch 32 with a single IGBT of sufficient stand-off voltage. Or, additional semiconductor switches may be incorporated in each leg to reduce the voltage that must be switched by each switch. To minimize the size and weight of the resulting output circuit 14, however, the construction described above is preferable. Consequently, within the scope of the appended claims, it will be appreciated that the invention can be practiced otherwise than as specifically described herein.

The embodiments of the inventions in which an exclusive property or privilege is claimed are defined as follows:

1. In an external defibrillator for applying a biphasic defibrillation pulse to a patient through first and second electrodes when said first and second electrodes are coupled to a patient, said external defibrillator including an energy storage capacitor having first and second leads and a charging system for charging said energy storage capacitor, said external defibrillator also including an H-bridge output circuit with four legs for switchably coupling the energy storage capacitor to the first and second electrodes in order to conduct the energy stored in the energy storage capacitor to a patient, a first switch in the first leg of the H-bridge output circuit coupled between the first lead of the energy storage capacitor and the first electrode, a second switch in the second leg of the H-bridge output circuit coupled between the second lead of the energy storage capacitor and the second electrode, a third switch in the third leg of the H-bridge output circuit coupled between the first lead of the energy storage capacitor and the second electrode, and a fourth switch in the fourth leg of the H-bridge output circuit coupled between the second lead of the energy storage capacitor in the first electrode, said external defibrillator further comprising a control circuit coupled to said first, second, third, and fourth switches for controlling said first, second, third, and fourth switches, the control circuit placing the first and second switches in a conducting state for a first period to conduct energy stored in the energy storage capacitor to the first and second electrodes and thereby generate the first phase of a biphasic defibrillation pulse for application to a patient, the control circuit placing the third, and fourth switches in a conducting state for a second period to conduct energy stored in the energy storage capacitor to the first and second electrodes and thereby generate the second phase of a biphasic defibrillation pulse for application to a patient, the improvement comprising:

(i) causing said charging system to charge said energy storage capacitor to a charge level of at least approximately 200 joules; and (ii) forming said first, second, third, and fourth switches of components capable of delivering at least approximately 200 joules to the first and second electrodes for application to a patient.

2. The improvement claimed in claim 1, wherein each of the first, third, and fourth switches comprise a silicon controlled rectifier (SCR) having a gate, an anode, and a cathode, the gate being connected for receiving gate signals, the anode and cathode being connected in a circuit path that provides current through the SCR.

3. The improvement claimed in claim 2, wherein said control circuit includes a plurality of gate drive circuits, each of the plurality of gate drive circuits coupled to the gate of one of each of the SCRs.

4. The improvement claimed in claim 3, wherein a gate signal supplied by each gate drive circuit to the gate of each SCR biases the SCR in the conducting state, the SCR remaining biased in the conducting state as long as the gate signal is present.

5. The improvement claimed in claim 4, wherein each gate drive circuit produces a pulse train and supplies said pulse train to the gate of each SCR as a gate signal.

6. The improvement claimed in claim 2, wherein the second switch comprises a plurality of insulated gate bipolar transistors (IGBTs) coupled in series, each IGBT having a gate, a collector, and an emitter, the gate being connected for receiving gate signals, the collector and emitter being connected in a circuit path to provide current through the IGBT.

7. The improvement claimed in claim 6, wherein said control circuit includes a gate drive circuit coupled to the gate of each of the plurality of IGBTs, the gate drive circuit providing a gate signal to the gate of each of the IGBTs for switching the plurality of IGBTs between a conducting state and a non-conducting state.

8. The improvement claimed in claim 7, wherein the gate drive circuit includes circuitry for controlling the switching speed of the plurality of IGBTs between the conducting state and the non-conducting state.

9. The improvement claimed in claim 8, wherein: (i) the gate drive circuit includes a plurality of capacitors coupled to the gates of the plurality of IGBTs, (ii) and the time required for the plurality of IGBTs to turn-on, i.e., enter the conducting state, is determined by the time it takes to charge the plurality of capacitors to a set voltage.

10. The improvement claimed in claim 9, wherein the turn-on time of the plurality of IGBTs is such that the IGBTs are turned on without spuriously turning on any of the SCRs.

11. The improvement claimed in claim 8, wherein the gate drive circuit includes a shunt coupled between the gate of each of the plurality of IGBTs and ground, the shunt acting to shunt a voltage applied to the gates of the plurality of IGBTs to ground.

12. The improvement claimed in claim 7, wherein the gate drive circuit supplies a gate signal that maintains the plurality of IGBTs in a saturated state when the IGBTs are in the conducting state.

13. The improvement claimed in claim 1, wherein the control circuit places the first switch and the fourth switch in a conducting state to shunt energy from the energy storage capacitor.

14. The improvement claimed in claim 1, wherein the control circuit places the second switch and the third switch in a conducting state to shunt energy from the energy storage capacitor.

15. The improvement claimed in claim 1, further comprising a protective component coupled between the energy storage capacitor and the H-Bridge output circuit, the protective component having resistive properties so as to limit a current to at least one of the first, second, third, or fourth switches.

16. The improvement claimed in claim 1, further comprising a protective component coupled between the energy storage capacitor and the H-Bridge output circuit, the protective component having inductive properties so as to limit a rise time of the voltage across at least one of the first, second, third, or fourth switches.

17. The improvement claimed in claim 1, further comprising a protective component coupled between the energy storage capacitor and the H-Bridge output circuit, the first, second, third, and fourth switches having a voltage across them that has a rise time that is determined by the amount of time it takes for the voltage across the switches to develop to a selected level, the protective component having both inductive and resistive properties so as to limit a current to, and a rise time of the voltage across at least one of the first, second, third, or fourth switches.

18. The improvement claimed in claim 1, further comprising a charging means for charging the energy storage capacitor wherein said first, second, third, and fourth switches are capable of conducting a first biphasic defibrillation pulse of approximately 200 joules to a patient after which the energy storage capacitor is recharged by the charging means and the first, second, third, and fourth switches are capable of conducting a second biphasic defibrillation pulse of approximately 360 joules to a patient.

19. The improvement of claim 1, wherein the capacitance of the energy storage capacitor lies in the range from 150 microfarads to 200 microfarads.

20. In an external defibrillator for applying a biphasic defibrillation pulse to a patient through a pair of electrodes when said pair of electrodes are coupled to a patient, said external defibrillator including an energy storage capacitor having first and second leads, said external defibrillator also including an H-bridge output circuit having four legs for switchably coupling the energy storage capacitor to the pair of electrodes in order to conduct the energy stored in the energy storage capacitor to the pair of electrodes for application to a patient and a control circuit for controlling the operation of said H-bridge output circuit, the improvement comprising an improved H-bridge output circuit and an improved control circuit, said improved H-bridge output circuit comprising:

(a) a first silicon controlled rectifier (SCR) in the first leg of the H-bridge output circuit coupled between the first lead of the energy storage capacitor and one of the pair of electrodes;

(b) an insulated gate bipolar transistor (IGBT) in the second leg of the H-bridge output circuit coupled between the second lead of the energy storage capacitor and the other of the pair of electrodes;

(c) a second SCR in the third leg of the H-bridge output circuit coupled between the first lead of the energy storage capacitor and the other of the pair of electrodes; and (d) a third SCR in the fourth leg of the H-bridge output circuit coupled between the second lead of the energy storage capacitor and the one of the pair of electrodes; and said improved control circuit controlling the first, second, and third SCRs and the IGBT, such that: (i) the first SCR and the IGBT are placed in a conducting state for a first period to conduct energy stored in the energy storage capacitor to the pair of electrodes for application to a patient and thereby generate a first phase of a biphasic defibrillation pulse; and (ii) the second, and third SCRs are placed in a conducting state for a second period to conduct energy stored in the energy storage capacitor to the pair of electrodes for application to a patient and thereby generate a second phase of said biphasic defibrillation pulse that is opposite in polarity to the first phase of said biphasic defibrillation pulse.

21. The improvement claimed in claim 20, wherein said improved control circuit includes first, second, and third gate drive circuits, the first, second, and third SCRs having gates, the first gate drive circuit being coupled to the gate of the first SCR, the second gate drive circuit being coupled to the gate of the second SCR, and the third gate drive circuit being coupled to the gate of the third SCR.

22. The improvement claimed in claim 21, wherein gate signals supplied by the first, second, and third gate drive circuits to the gate of the associated SCR biases the associated SCR in the conducting state, the associated SCR remaining biased in the conducting state as long as the gate signal is present.

23. The improvement claimed in claim 22, wherein each gate drive circuit includes a means for producing a pulse train and a means for supplying said pulse train to the gate of each SCR as a gate signal.

24. The improvement claimed in claim 20, wherein the second leg of the H-bridge output circuit includes more than one IGBTs, each of said more than one IGBTs having a gate and said improved control circuit includes a gate drive circuit coupled to a gate of each of the more than one IGBTs, the gate drive circuit providing a gate signal to the gate of each of the more than one IGBTs for switching the more than one IGBTs between a conducting state and a non-conducting state.

25. The improvement claimed in claim 24, wherein the gate drive circuit includes circuitry for controlling the switching speed of the more than one IGBTs between the conducting state and the non-conducting state.

26. The improvement claimed in claim 25, wherein the gate drive circuit includes more than one capacitors, each of the capacitors coupled to a gate of a respective one of the IGBTs, the time required for the respective one of the IGBTs to turn-on i.e., enter the conducting state, being the time it takes for the capacitors to be charged to a set voltage.

27. The improvement claimed in claim 26, wherein the turn-on time of the more than one IGBTs is such that the more than one IGBTs are turned on without spuriously turning on any of the SCRs.

28. The improvement claimed in claim 24, wherein the gate drive circuit supplies a gate signal that maintains the more than one IGBTs in a saturated state when the more than one IGBTs are in the conducting state.

29. The improvement claimed in claim 24, wherein the gate drive circuit includes a shunt coupled between the gate of each of the more than one IGBTs and ground, the shunt acting to shunt a voltage applied to the gates of the more than one IGBTs to ground.

30. The improvement claimed in claim 20, wherein the improved control circuit places the first SCR and the third SCR in a conducting state to shunt energy from the energy storage capacitor.

31. The improvement claimed in claim 20, wherein the improved control circuit places the IGBT and the second SCR in a conducting state to shunt energy from the energy storage capacitor.

32. The improvement claimed in claim 20, the improvement further comprising a protective component between the energy storage capacitor and the H-bridge output circuit, the protective component having resistive properties so as to limit a current to at least one of the first, second, or third SCRs, or the IGBT.

33. The improvement claimed in claim 20, the improvement further comprising a protective component coupled between the energy storage capacitor and the H-bridge output circuit, the protective component having inductive properties so as to limit a rise time of the voltage across at least one of the first, second, or third SCRs, or the IGBT.

34. The improvement claimed in claim 20, the improvement further comprising a protective component coupled between the energy storage capacitor and the H-bridge output circuit the first, second, and third SCRs and the IGBT having a voltage across them that has a rise time that is determined by the amount of time it takes for the voltage across the switches to develop to a selected level the protective component having both inductive and resistive properties so as to limit a current to, and a rise time of the voltage across, at least one of the first, second, or third SCRs, or the IGBT.

35. The improvement claimed in claim 20, wherein the improved H-bridge output circuit further comprises a charging means for charging the energy storage capacitor wherein the conducting states of the first, second, and third SCRs and the IGBT of the output circuit provide at least a first biphasic defibrillation pulse of approximately 200 joules to said pair of electrodes for application to a patient after which the energy storage capacitor is recharged by the charging means, and the conducting states of the first, second and third SCRs and the IGBT of the output circuit provide a second biphasic defibrillation pulse of approximately 360 joules to said pair of electrodes for application to a patient.

36. The improvement of claim 20, wherein the capacitance of the energy storage capacitor lies in the range from 150 microfarads to 200 microfarads.

37. In an external defibrillator for applying a biphasic defibrillation pulse to a patient through first and second electrodes when said first and second electrodes are coupled to a patient, said external defibrillator including an energy storage capacitor having first and second leads, said external defibrillator also including an H-bridge output circuit having four legs each including one or more solid state switches for switchably coupling the energy storage capacitor to the first and second electrodes in order to conduct the energy stored in the energy storage capacitor to the first and second electrodes for application to a patient, the improvement comprising a drive circuit for said solid state switches that maintains said solid state switches in a conducting state at low defibrillation pulse energy levels such as the defibrillation pulse energy levels used in surgery to directly defibrillate a patient.

38. The improvement claimed in claim 37, wherein the low defibrillation pulse energy level is less than 50 joules.

39. The improvement claimed in claim 37, wherein the solid state switches each have a gate that is coupled to receive gate signals and wherein the gate drive circuit produces a pulse train and supplies said pulse train to the gates of the solid state switches.

40. The improvement claimed in claim 39, wherein at least one of said solid state switches comprises a silicon controlled rectifier (SCR).

41. The improvement claimed in claim 37, wherein the H-bridge output circuit is capable of switching defibrillation pulses over a range that extends from below 50 joules to above 200 joules.

42. In an external defibrillator for applying a defibrillation pulse to a patient through a pair of electrodes when said electrodes are coupled to a patient, said external defibrillator including a housing and defibrillator circuitry for providing defibrillation pulses and control circuitry for controlling the operation of said defibrillator circuitry, said control circuitry including control knobs mounted in said housing, the improvement comprising isolation circuitry for isolating said control circuitry and, thus, said housing from said defibrillator circuitry.

43. The improvement claimed in claim 42, wherein the isolation circuitry comprise a plurality of transformers each of said transformers having primary and secondary windings, the primary windings being coupled to the control circuitry and the secondary windings being coupled to the defibrillator circuitry.

44. The improvement claimed in claim 43, wherein said defibrillation circuitry includes: (i) a high voltage energy storage capacitor having first and second leads and a pair of electrodes; and (ii) an output circuit for selectively, switchably coupling the leads of said high voltage energy storage capacitor to said pair of electrodes, said output circuit comprising:

(a) a first switch coupled between the first lead of the energy storage capacitor and the first electrode;

(b) a second switch coupled between the second lead of the energy storage capacitor and the second electrode;

(c) a third switch coupled between the first lead of the energy storage capacitor and the second electrode; and (d) a fourth switch coupled between the second lead of the energy storage capacitor and the first electrode; and wherein said control circuitry controls said first, second, third, and fourth switches by applying control signals to the primary windings of said plurality of transformers.

45. In an external defibrillator for applying a biphasic defibrillation pulse to a patient through first and second electrodes when said first and second electrodes are coupled to the patient, said external defibrillator including an energy storage capacitor having first and second leads, said external defibrillator also including an H-bridge output circuit having four legs for switchably coupling the first and second leads of the energy storage capacitor to the first and second electrodes in order to conduct the energy stored in the energy storage capacitor to the first and second electrodes for application to a patient, a first switch in the first leg of the H-bridge output circuit coupled between the first lead of the energy storage capacitor and the first electrode, a second switch in the second leg of the H-bridge output circuit coupled between the second lead of the energy storage capacitor and the second electrode, a third switch in the third leg of the H-bridge output circuit coupled between the first lead of the energy storage capacitor and the second electrode, a fourth switch in the fourth leg of the H-bridge output circuit coupled between the second lead of the energy storage capacitor and the first electrode, the improvement comprising: (i) at least one of the first, second, third, or fourth switches including an isolated gate bipolar transistor (IGBT); and (ii) a gate drive circuit, the gate drive circuit biasing the gate of the IGBT with sufficient voltage for the IGBT to be able to withstand a current pulse of up to 400 amps without damage to the IGBT.

46. The improvement of claim 45, wherein the gate drive circuit only biases the IGBT with sufficient voltage for the IGBT to be able to withstand a defibrillation current pulse of up to 400 amps without damage to the IGBT for brief intervals.

47. In an external defibrillator for applying a biphasic defibrillation pulse to a patient through first and second electrodes when said first and second electrodes are coupled to a patient, said external defibrillator including an energy storage capacitor having first and second leads, said external defibrillator also including an H-bridge output circuit with four legs for switchably coupling the energy storage capacitor to the first and second electrodes in order to conduct the energy stored in the energy storage capacitor to the first and second electrodes for application to a patient, a first switch in the first leg of the H-bridge output circuit coupled between the first lead of the energy storage capacitor and the first electrode, a second switch in the second leg of the H-bridge output circuit coupled between the second lead of the energy storage capacitor and the second electrode, a third switch in the third leg of the H-bridge output circuit coupled between the first lead of the energy storage capacitor and the second electrode, a fourth switch in the fourth leg of the H-bridge output circuit coupled between the second lead of the energy storage capacitor and the first electrode, the improvement comprising: (i) at least one of the first, second, third, or fourth switches of the H-bridge output circuit including a silicon controlled rectifier (SCR), and at least one other of the first, second, third, or fourth switches including an insulated gate bipolar transistor (IGBT); and (ii) a gate drive circuit connected to said IGBT for turning on said IGBT at a rate that is slow enough to prevent the SCR from spuriously firing.

* * * * *